US006488709B1

(12) United States Patent
Barrett

(10) Patent No.: US 6,488,709 B1
(45) Date of Patent: Dec. 3, 2002

(54) INTRAOCULAR LENS IMPLANT

(76) Inventor: Graham David Barrett, 56 Dampier Avenue, City Beach, Western Australia 6015 (AU)

( * ) Notice: Subject to any disclaimer, the term of this patent is extended or adjusted under 35 U.S.C. 154(b) by 0 days.

(21) Appl. No.: 09/743,154

(22) PCT Filed: Jul. 6, 1999

(86) PCT No.: PCT/AU99/00544

§ 371 (c)(1),
(2), (4) Date: Jan. 5, 2001

(87) PCT Pub. No.: WO00/01323

PCT Pub. Date: Jan. 13, 2000

(30) Foreign Application Priority Data

Jul. 6, 1998 (AU) ............................................... PP4500

(51) Int. Cl.$^7$ .................................................. A61F 2/16
(52) U.S. Cl. ..................... 623/6.43; 623/6.46; 623/6.39
(58) Field of Search ............................... 623/6.11, 6.38, 623/6.39, 6.4, 6.43, 6.46

(56) References Cited

U.S. PATENT DOCUMENTS

| 4,463,458 A | * | 8/1984 | Seidner ..................... 623/6.11 |
| 4,551,864 A | * | 11/1985 | Akhavi ..................... 623/6.11 |
| 4,605,410 A | * | 8/1986 | Grendahl ................... 623/6.11 |
| 4,678,469 A | * | 7/1987 | Kelman ..................... 623/6.11 |
| 4,932,967 A | | 6/1990 | Kansas ........................... 623/6 |
| 4,950,288 A | | 8/1990 | Kelman ........................... 623/6 |
| 5,071,432 A | * | 12/1991 | Baikoff ..................... 623/6.11 |
| 6,171,337 B1 | * | 1/2001 | Galin ......................... 623/6.11 |
| 6,179,870 B1 | * | 1/2001 | Sourdille et al. ........... 623/6.11 |
| 6,200,343 B1 | * | 3/2001 | Anschutz ................... 623/6.11 |
| 6,228,115 B1 | * | 5/2001 | Hoffmann et al. ......... 623/6.11 |

FOREIGN PATENT DOCUMENTS

| EP | 0195881 | 10/1986 |
| EP | 0766952 | 4/1997 |
| WO | 9712564 | 4/1997 |
| WO | 9805273 | 2/1998 |

OTHER PUBLICATIONS

Derwent WPAT Online Accession No. 95–240882/31 relating to ZA9405507A.

* cited by examiner

Primary Examiner—Dinh X. Nguyen
(74) Attorney, Agent, or Firm—Howard & Howard

(57) ABSTRACT

An intraoocular lens implant (10) including an optic (12) and a haptic (20). The haptic (20) includes a first portion (22) extending outwardly in a first direction from the optic (12), a second portion (26) which has an outermost end (32), extending outwardly in a second opposing direction to the first portion (22), and a bend member (24) intermediate and interconnecting the first portion (22) and the second portion (26). An end of the first portion (22) remote from the bend member (24) is connected to the optic (12) at a haptic optic junction (29) and the outermost end (32) of the second portion (26) is located on a side of the haptic optic junction (29) opposite to the side on which the bend member (24) is located.

12 Claims, 1 Drawing Sheet

INTRAOCULAR LENS IMPLANT

FIELD OF THE INVENTION

The present invention relates to an intraocular lens implant.

BACKGROUND OF THE INVENTION

The crystalline lens is a transparent structure that focuses light in the human eye. Opacification of the lens known as cataract formation is a common cause of poor vision in the elderly, and can be corrected surgically.

Modern cataract surgery is performed by manual extracapsular cataract extraction, or by phacoemulsification. Manual extracapsular cataract extraction involves expressing the hard nucleus of the cataract through a 10 mm to 12 mm incision. Phacoemulsification utilises ultrasonic energy transmitted by a needle to fragment the nucleus and allow aspiration of the cataract through a 2.8 mm to 3.2 mm incision. In both operations an opening is made in the anterior capsule to allow removal of the lens contents. The capsular bag remnant, however, is left in situ to provide support for an intraocular lens implant which is inserted following removal of the cataract to replace the focussing power of the natural crystalline lens.

It is known to provide an intraocular lens implant which typically comprises a central focusing element, known as the optic, and a peripheral support structure, known as the haptic. The optic and the haptic of the intraocular lens may be manufactured from transparent rigid plastics material such as polymethyl methacrylate, or from flexible plastics material such as silicone or hydrogel. Intraocular lens implants manufactured from flexible material are preferable to those made of rigid material because the lens may be folded to allow insertion through a small incision in the sclera or outercoat of the eye and is then required to unfold to its original dimension.

The optic and haptic of the intraocular lens may be manufactured from the same material as a single piece unit or the haptic may be attached to the optic by a variety of mechanisms. There may be one or a plurality of haptics attached to the optic, although the most common configuration includes an optic with two outwardly extending haptics. The purpose of the haptic is to provide optimal centration of the optic as well as a means of fixation of the implant within a capsular bag remnant of the original lens following cataract or lens extraction. It is preferable that the haptics conform to the periphery of the capsular bag to provide a larger surface area of contact between the intraocular lens implant and the capsular bag and to ensure centration of the optic. It is also possible to implant a lens in front of the anterior capsule behind the iris with the haptics resting in the region between the root of the iris and ciliary processes, known as the cilairy sulcus. Intraocular lenses may also be inserted in phakic eyes to correct refractive errors, such as myopia or hyperopia, in front of the crystalline lens behind the iris with the haptic providing support in the cilairy sulcus. Furthermore, as an alternative site of implantation in phakic eyes, intraocular lenses may be inserted in front of the iris in the anterior chamber with the haptics resting in the angle of the anterior chamber.

In all these instances it is preferable that the haptics conform to the periphery of the capsular bag or to the cilairy sulcus, phakic eye or the angle of the anterior chamber. The prior art discloses several haptic designs, including a flange style or loop style, which seek to maximise the surface area of contact between the intraocular lens implant and the capsular bag. The most common design includes two loop style haptics attached at diametrically opposed points of an optic wherein terminal ends of the haptics extend arcuately towards the periphery of the capsular bag.

The fixation and stability of the intraocular lens implant is not solely dependent on the rigidity of the supporting haptics of an intraocular lens, but is also dependent on fusion of leaflets of anterior and posterior capsule in the interval between the optic of the implant and the terminal of the haptic in contact with the periphery of the capsular bag. It is preferable to maintain as large an interval as possible to provide maximum opportunity for fusion to occur.

Post-operative shrinkage of the capsular bag is not an unusual occurrence. The aforementioned interval may be maintained by a rigid haptic which resists shrinkage of the capsular bag, or by a design for haptics manufactured from flexible plastics which maintains an interval between the terminal of the haptic and the optic in the event of shrinkage of the capsular bag. In order that the design should accommodate the various sizes of capsular bag that will be encountered in different individuals as well as the varying degrees of shrinkage that would occur during the post-operative phase, it is preferable that the haptics should be compressible.

A distinct disadvantage, however, of the current haptic designs is that the haptic terminal may be flexed at any point between the haptic terminal and the haptic optic junction towards the optic such that the interval between the haptic terminal and the optic is reduced to the extent where migratory fusion of the leaflets of the anterior and posterior capsule fails to occur.

The present invention seeks to overcome the aforementioned disadvantages and provide better conformity of the terminal of the haptic with the periphery of the capsular bag, or to the ciliary sulcus, or to the angle of the anterior chamber. Since the greatest proportion of the intraocular lens implants are made with respect to a capsular bag remnant it is preferable that a haptic design should allow the terminal of the haptic to conform to the periphery of the capsular bag.

SUMMARY OF THE INVENTION

In accordance with one aspect of the invention there is provided an intraocular lens implant including an optic and a haptic, the haptic including a first portion extending outwardly in a first direction from the optic, a second portion which has an outermost end, extending outwardly in a second opposing direction to the first portion, and a bend member intermediate the first portion and the second portion, the bend member interconnecting the first portion and second portion, an end of the first portion remote from the bend member being connected to the optic at a haptic optic junction and the outermost end of the second portion being located on a side of the haptic optic junction opposite to the side on which the bend member is located.

BRIEF DESCRIPTION OF THE DRAWING

The present invention will now be described, by way of example, with reference to the accompanying drawing, in which.

DETAILED DESCRIPTION OF THE PREFERRED EMBODIMENT

Figure 1:
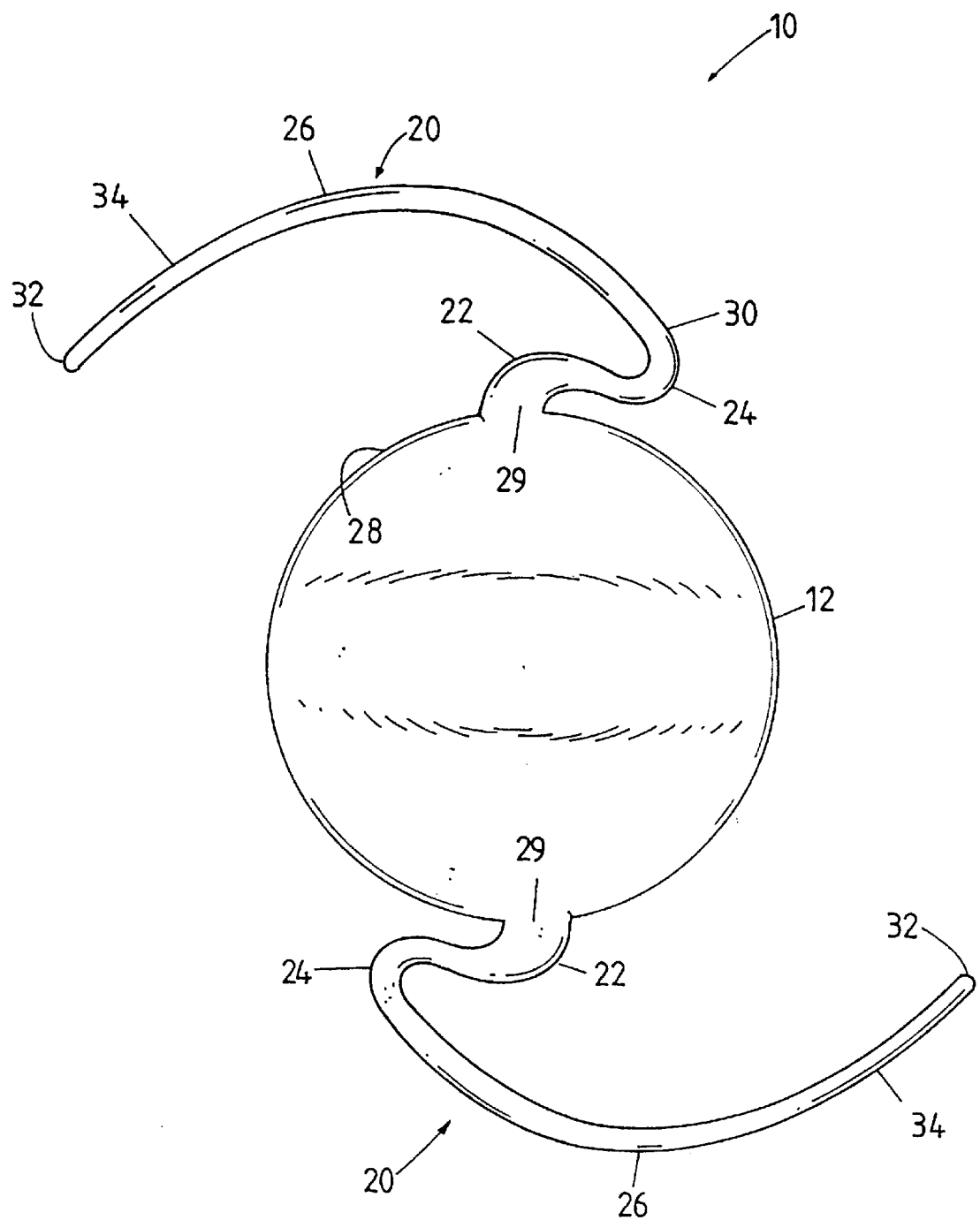
FIG. 1 is a plan view of an intraocular lens implant in accordance with the present invention including an optic and a pair of haptics.

In FIG. 1 of the accompanying drawing, there is shown an intraocular lens implant 10, including an optic 12 and a pair of haptics 20. The optic 12 is a substantially circular convex member and may be manufactured from polymethyl methacrylate, or preferably from flexible plastics material such as silicone or hydrogels.

The haptic includes a first portion 22 interconnected to a second portion 26 by an elbow-shaped bend 24. An end of the first portion 22 remote from the bend member 24 of the haptic 20 is attached to the circumferential surface 28 of the optic 12 at a haptic optic junction 29. The first portion 22 of the haptic 20 extends outwardly from the optic 12 in an arcuate manner in a clockwise direction.

The second portion 26 of the haptic 20 extends outwardly from the elbow-shaped bend 24 in an arcuate manner in an anticlockwise direction. In other embodiments of the invention it will be appreciated that, alternatively, the first portion 22 could extend outwardly from the optic 12 in an arcuate manner in an anti-clockwise direction and the second portion 26 could extend outwardly from the elbow-shaped bend 24 in an arcuate manner in a clockwise direction.

The haptic 20 may be manufactured from polymethyl methacrylate, or preferably from flexible plastic materials such as silicone or hydrogels.

Preferably, the first portions 22 of a pair of haptics 20 are attached to the circumferential surface 28 of the optic 12 at respective diametrically opposed locations. In other words, the haptic optic junctions 29 are spaced equiangularly around a circumferential surface 28 of the optic 12.

In use, the haptic facilitates optimal conformation of the haptic terminal with the capsular bag by providing two counterbalanced points for flexion to occur when the haptic is compressed by post-operative shrinkage of the capsular bag. This is achieved by a haptic which extends away from the optic in an arcuate manner and then reverses direction such that the loop or elbow formed by the change in direction is on the opposite side of the haptic-optic junction to the peripheral area of the contact of the distal loop with the capsular bag.

Compression of the second portion 26 of the haptic 20 at a flexion point 34 distal to the elbow-shaped bend 24 will tend to incline the terminal 32 of the haptic 20 towards the optic 12, thereby decreasing the interval between the optic 12 of the implant and the terminal 32 of the haptic 20 in contact with the periphery of the capsular bag. This tendency is counterbalanced in the present invention where compression of the second portion 26 of the haptic at a flexion point 30 proximal to the elbow-shaped bend 24 will tend to decrease the interval between the optic 12 of the implant and the elbow-shaped bend 24 of the haptic 20, resulting in an expansion of the peripheral arc of the second portion 26 of the haptic, thereby increasing the interval between the optic 12 of the implant and the terminal 32 of the haptic 20 in contact with the periphery of the capsular bag.

It is considered within the scope of the invention if one or a plurality of haptics are attached to the optic, and the terminals of the haptics extend in identical or opposite directions.

Modifications and variations as would be apparent to a skilled addressee are deemed to be within the scope of the present invention.

What is claimed is:

1. An intraocular lens implant comprising: an optic and a haptic including a first portion extending outwardly in a first direction from the optic and a second portion having an outermost end extending outwardly in a second direction opposite to the first direction and first portion, a bend member intermediate and interconnecting the first portion and second portion, said first portion having an end remote from the bend member and connected to the optic at a haptic optic junction, said second portion having an outermost end located on a side of the haptic optic junction opposite to the side on which the bend member is located, said second portion of the haptic including a first flexion point distal to the bend member and a second flexion point proximal to the bend member for counterbalancing compression at the first flexion point, that tends to incline the outermost end of the haptic towards the optic by compression at the second flexion point that tends to incline the bend member towards the optic to thereby maintain an interval between the outermost end of the haptic and the optic.

2. An intraocular lens implant according to claim 1, characterised in that the intraocular lens implant includes an optic and a plurality of haptics.

3. An intraocular lens implant according to claim 2, characterised in that the second portion of each haptic extends outwardly from the bend member, each second portion extending in the same rotational sense as all of the other second portions.

4. An intraocular lens implant according to claim 2, characterised in that the haptic optic junctions are spaced equiangularly around a circumferential surface of the optic.

5. An intraocular lens implant according to claim 2, characterised in that the first portion of the haptic extends outwardly from the optic in an arcuate manner.

6. An intraocular lens implant according to claim 2, characterised in that the second portion of the haptic extends outwardly from the bend member in an arcuate manner.

7. An intraocular lens implant according to claim 2, characterised in that the second portion of the haptic conforms with a periphery of an ocular substrate into which the intraocular lens has been implanted, so as to provide a substantial area of contact between the intraocular lens implant and the ocular substrate.

8. An intraocular lens implant according to claim 7, characterised in that the second portion of the haptic conforms to the periphery of a capsular bag.

9. An intraocular lens implant according to claim 2, characterised in that the haptic is formed of a flexible plastics material.

10. An intraocular lens implant according to claim 2, characterised in that the optic is formed of a flexible plastics material.

11. An intraocular lens implant according to claim 2, characterised in that the bend member is elbow-shaped.

12. An intraocular lens implant according to claim 2, characterised in that the haptic is integral with the optic.

\* \* \* \* \*